United States Patent
Klein

(10) Patent No.: US 8,167,866 B2
(45) Date of Patent: May 1, 2012

(54) DRUG DELIVERY SYSTEM FOR ACCELERATED SUBCUTANEOUS ABSORPTION

(76) Inventor: Jeffrey A. Klein, San Juan Capistrano, CA (US)

( * ) Notice: Subject to any disclaimer, the term of this patent is extended or adjusted under 35 U.S.C. 154(b) by 0 days.

(21) Appl. No.: 12/415,233

(22) Filed: Mar. 31, 2009

(65) Prior Publication Data

US 2010/0249746 A1   Sep. 30, 2010

Related U.S. Application Data

(63) Continuation of application No. 10/877,337, filed on Jun. 25, 2004, now Pat. No. 7,572,613.

(51) Int. Cl.
*A61M 37/00* (2006.01)
(52) U.S. Cl. .................. 604/511; 435/183
(58) Field of Classification Search .......... 604/507, 604/518, 20, 82, 92; 424/94.91, 449
See application file for complete search history.

(56) References Cited

U.S. PATENT DOCUMENTS

| | | | |
|---|---|---|---|
| 5,750,141 A * | 5/1998 | Roberts et al. | 424/449 |
| 6,258,791 B1 | 7/2001 | Braun | |
| 6,296,847 B1 | 10/2001 | Gokcen et al. | |
| 6,315,756 B1 | 11/2001 | Tankovich | |
| 6,562,054 B1 | 5/2003 | Weber et al. | |
| 6,565,541 B2 | 5/2003 | Sharp | |
| 7,465,291 B2 | 12/2008 | Massengale | |
| 2004/0106904 A1 * | 6/2004 | Gonnelli et al. | 604/173 |
| 2004/0127425 A1 | 7/2004 | Nudler et al. | |
| 2004/0199209 A1 * | 10/2004 | Hill et al. | 607/3 |
| 2004/0268425 A1 * | 12/2004 | Bookbinder et al. | 800/18 |

* cited by examiner

*Primary Examiner* — Kevin C Sirmons
*Assistant Examiner* — Brandy C Scott
(74) *Attorney, Agent, or Firm* — Stetina Brunda Garred & Brucker

(57) ABSTRACT

A method for accelerating subcutaneous absorption of a fluid or drug into the systemic circulation of a specific targeted tissue. A first drug operative to produce local capillary vasodilatation and/or increase the rate of bulk flow of solution through the interstitial space is mixed with a fluid. The fluid may contain a crystalloid solution or a dilute solution of a pharmacologic drug required for a routine or emergency therapeutic treatment for a patient. The first drug is substantially non-toxic to the patient. The fluid mixed with the first drug is then delivered subcutaneously or into deeper tissues of the patient, by use of a hyperdermic needle or infiltration cannula. As the capillaries are dilated, the fluid is efficiently absorbed and circulated systemically.

7 Claims, 2 Drawing Sheets

DRUG DELIVERY SYSTEM FOR ACCELERATED SUBCUTANEOUS ABSORPTION

CROSS-REFERENCE TO RELATED APPLICATIONS

This application is a continuation application of U.S. patent application Ser. No. 10/877,337, filed Jun. 25, 2004, now U.S. Pat. No. 7,572,613.

The subject application is related to Applicant's pending U.S. patent application Ser. No. 10/877,566, filed Jun. 25, 2004 entitled INFILTRATION CANNULA, the disclosure of which is expressly incorporated herein by reference.

STATEMENT RE: FEDERALLY SPONSORED RESEARCH/DEVELOPMENT

Not Applicable

BACKGROUND OF THE INVENTION

The present invention relates in general to accelerated subcutaneous absorption, and more particularly, to a method that accelerates drug absorption rates with minimal toxicity.

By way of background and to better facilitate a complete understanding of the present invention the following terms shall have the following definitions:

Solvent: A substance (usually a liquid) having the power to dissolve other substances. In the present application, both water and commercially available crystalloids (e.g. 0.9% sodium chloride/physiologic saline or lactated Ringer's solution) are considered to be exemplary solvents.

Solute: The dissolved substance, the substance dissolved by the solvent in a solution. In the present application, preferable solutes include pharmaceutical drugs such as methyl nicotinamide, hyaluronidase, lidocaine, and epinephrine, that are dissolved in a crystalloid solvent.

Solution: The action of changing from a solid or gaseous state to a liquid state, the state of being desolved.

Tumescent Technique or Tumescent Infiltration are defined as a method of subcutaneous drug delivery of large volumes of very dilute medication together with dilute epinephrine in isotonic solution of crystalloid (e.g., physiologic saline, lactated Ringer's solution, Hartman's solutions, etc.) infiltrated directly into subcutaneous fat or muscle or along the exterior length of a vein to produce swelling and firmness, or tumescence, of the targeted tissues, and thus produce very slow systemic absorption as a result of intense subcutaneous vasoconstriction, as well as direct hydrostatic compression of capillaries and veins. Tumescent Drug Delivery, or Tumescent Delivery are synonyms that refer to the tumescent technique for delivering a drug into the subcutaneous space. In other words, tumescent delivery is a process of infiltration of very large volumes of very dilute solutions of therapeutic substances dissolved in a crystalloid solution into subcutaneous tissue to the point of producing tumescence of the targeted tissue. Drugs other than lidocaine can be administered by means of tumescent delivery, that is, by subcutaneous infiltration of extremely dilute drug, with or without a vasoconstrictor such as epinephrine.

Tumescent and tumescence are synonyms for swollen and firm.

Tumescent liposuchtion is defined as liposuction performed totally by local anesthesia using tumescent local anesthesia.

Tumescent fluid and/or tumescent solution are defined as dilute solutions of therapeutic substances dissolved in a crystalloid solution intended for tumescent delivery into subcutaneous tissue.

Tumescent "drug": the "drug" in the context as an ingredient in a tumescent solution and its pharmacokinetic behavior as a result of the pharmacokinetics of a tumescent solution; for example tumescent lidocaine, tumescent epinephrine, tumescent antiobiotic.

Tumescent Local Anesthesia (TLA) is local anesthesia produced by direct infiltrations into subcutaneous tissues of large volumes of very dilute lidocaine (e.g., less than or equal to 1 gram/liter) and epinephrine (e.g., less than or equal to 1 milligram/liter) with sodium bicarbonate (e.g., 10 milliequivalents/liter) in a crystalloid solution such as physiologic saline (NaCl) or lactated Ringer's solution. Although higher concentrations can be used and still qualify as TLA, it is generally safer to use the least (lowest) effective concentration.

Tumescent Local Anesthetic Solution (TLA Solution) is the local anesthetic solution used to produce TLA. Typically, a TLA Solution consists of a 10 to 20 fold dilution of commercially available concentration of lidocaine and epinephrine. Thus, a commercial solution of lidocaine and epinephrine contains 10 grams of lidocaine per liter (10 gm/L) and 10 milligrams of epinephrine per liter. In contrast TLA Solution typically contains very dilute lidocaine ($\leq 1$ gram/liter) and epinephrine ($\leq 1$ milligram/liter) with sodium biocarbonate (10 milliequivalents/liter) in a crystalloid solution such as physiologic saline or lactated Ringer's solution. Typically the volume of infiltrated TLA Solution is so large that the skin and subcutaneous tissue becomes tumescent, in other words swollen and firm.

Tumescent Pharmacokinetics is defined as the absorption pharmacokinetics [the pharmacologic and physiologic factors associated with the systemic absorption of a drug] after tumescent infiltration of a drug is dramatically slower than the rate of systemic absorption of routine injection of the drug. The intense vasoconstriction induced by epinephrine, slows the rate of drug absorption into the central circulation and prolongs the local effects of the drug. For example, the duration of local anesthesia with lidocaine is typically 2 hours, in contrast the duration of local anesthesia with tumescent local anesthesia is 12 to 18 hours or more. A similar prolonged effect of tumescent antibiotic infiltration significantly improves the prophylactic effect of preoperative antibiotic therapy in the prevention of surgical site infections.

Bulk flow: The physical flow of a volume of fluid through a space, for example, water flowing through a sieve or strainer. Water flowing through the interstitial space between cells of a tissue is one example of the phenomenon of bulk flow in physiology.

In clinical situations such as severe trauma, hypoglycemia or dehydration which requires an immediate systemic administration of fluids or drugs, the most effective mode of delivery is often an intravenous (IV) infusion. However, IV infusion is not always easily accomplished or possible, in particular when the veins of a patient are difficult to locate due to severe dehydration or when ambient light is so low that the veins of the patient are not visible. Further, substantial clinical skills are typically required for gaining IV access. Therefore, during an emergency situation in isolated areas far from trained medical clinicians, IV administration of drugs may not be possible. As such, often times patients must wait until trained clinicians and proper facilities are available to insert and establish secure IV access. However any significant delay in establishing an IV site and administrating required drugs can have serious adverse consequences. Thus, there exists a substantial need in the art for a simple, safe technique that can be performed by a layman and which produces a rapid systemic administration of a drug or a fluid applied to a patient by subcutaneous infiltration or topical application.

Although not by way of limitation, the present invention is specifically suited for use with Applicant's Infiltration Cannula disclosed in pending U.S. patent application Ser. No. 10/877,566, filed Jun. 25, 2004 entitled INFILTRATION CANNULA, the disclosure of which is expressly incorporated herein by reference as disclosed therein A suitable Infiltration Cannula consists of a flexible plastic cannula (approximately 15 to 20 cm long) with holes (apertures) arranged along the distal 90% of the flexible cannula, and through which tumescent fluid can be rapidly delivered to subcutaneous tissue or muscle. Known as Kleinfiltrator™ cannulas, these flexible infiltration cannulas provide a means for relatively rapid fluid resuscitation in emergency situations when establishing an intravenous (IV) access is not feasible. These flexible infiltration cannulas have important applications in treating wounded soldiers in night-time combat conditions when establishing an IV access in total darkness is nearly impossible without using a flash light, and using a flash light might attract deadly enemy fire. Such flexible infiltration cannulas also have important applications in treating mass-casualty victims suffering hypovolemia as a result of epidemic infections, biologic warfare, or trauma such as explosions, burns, radiation exposure, or earthquake associated injury. Such flexible infiltration cannulas also have applications in surgical patients wherein the surgeon can provide localized preoperative preemptive analgesia and simultaneously provide tumescent delivery of a prophylactic dose of an antibiotic aimed precisely at tissues targeted for surgical intervention.

The present invention comprises a method of accelerated subcutaneous absorption, which is intended to act in concert with such flexible infiltration cannula or other suitable infiltration cannula. Such infiltration cannulas allow rapid tumescent infiltration of a large volume of crystaloid solution (possibly containing additional therapeutic drugs) into subcutaneous tissue or muscle. The method of accelerated systemic absorption of fluid then provides a means of maximizing the delivery of the tumescent solution to the systemic circulation.

BRIEF SUMMARY OF THE INVENTION

The present invention provides a drug delivery system and method for accelerating subcutaneous absorption of a fluid or drug. The method comprises the use of a first drug, operative to produce local capillary vasodilatation and/or augmented rate of bulk flow, which is mixed with a fluid. The fluid may include a specific crystalloid solution or a dilute solution of a pharmacologic drug required under a clinical emergency of a patient. The first drug is substantially non-toxic to the patient. The fluid mixed with the first drug is then subcutaneously delivered to the patient. By way of example and not limitation, suitable examples of the first drug include methyl-nicotinamide, methyl-nicotinate or hyaluronidase. Exemplary fluids include physiologic saline, lactated Ringer's solution or a dilute solution of pharmacologic drug such as an antibiotic.

Preferably, the fluid mixed with the first drug is delivered to the patient by subcutaneous infiltration. The subcutaneous infiltration can be performed by inserting an infiltration cannula under the skin of the patient, followed by infiltrating the fluid mixed with the first drug into subcutaneous tissue of the patient through the infiltration cannula. Preferably but optionally, a plastic Kleinfiltrator™ cannula is used as the infiltration cannula, such that a layman can easily perform the infiltration of the fluid.

In the first preferred embodiment of the present invention, a first drug is added a tumescent solution which produces an augmented rate of systemic absorption of the solvent (physiologic 0.9% sodium chloride or lactated Ringer's solution) and/or an additional second therapeutic drug (such as an antibiotic) also contained in the solution, when the tumescent solution is injected into the subcutaneous tissue or muscle. The first drug can act to produce either an increased degree of capillary vasodilation (for example methylnicotinc acid or nicotinamide) and thereby increase the rate of diffusion of the solvent and/or second therapeutic drug across the capillary wall and into the systemic circulation, or the first drug can act as an agent to increase the rate of bulk flow of fluid through the interstitial gel substance (for example hyaluronidase) and thereby hasten the spread of the tumescent fluid throughout a larger volume of tissue and thus accelerate systemic absorption.

In a second embodiment of this invention, two separate solutions of tumescent fluid are injected into the subcutaneous tissue at different depths permitting a clinician to preferentially cause a first drug to selectively flow toward and be absorbed into a specific subcutaneous tissue or cutaneous tissue.

For example, a first solution containing a vasoconstrictive drug (such as epinephrine or vasopressin) may be injected into a relatively deep plane of the subcutaneous tissue. Then a second solution containing a therapeutic drug is injected into a more superficial subcutaneous plane. Thus, the first vasoconstrictive tumescent fluid acts as an agent to provide a buffer that prevents or delays absorption of the second drug into deeper tissues of the patient. Alternatively, the vasoconstrictive solution is injected first into the subcutaneous tissue immediately subjacent to the skin, and then the second solution containing the therapeutic drug is injected into a deeper subcutaneous plane. Thereby, a buffer is provided to prevent or delay absorption of the second drug into the superficial subcutaneous tissue or skin of the patient.

The second embodiment of the present invention further comprises a method of increasing the absorption rate of a therapeutic drug, in which a first solution is applied in a first level under skin of a patient, and a second solution is applied to a second level under skin of the patient. The first solution preferably contains the therapeutic drug for treating the skin of the patient, and the second solution preferably contains a vasoconstrictive drug only. The second level is deeper than the first level to serve as a buffer for preventing or delaying absorption of the therapeutic drug into deep vascular tissue. Preferably, the first solution further contains a vasodilation drug, and the vasoconstrictive drug includes epinephrine or vasopressin.

As is well known, in the original version of the tumescent technique, invented by the subject applicant Jeffrey A. Klein, M.D., epinephrine was added to physiologic saline in order to delay the systemic absorption of the physiologic saline and a second solute, lidocaine. The vasoconstriction provided by dilute epinephrine produced both profound surgical hemostasis and significantly delayed lidocaine absorption to which prolong local anesthesia. By combining lidocaine and epinephrine in physiologic saline, the subject applicant facilitated liposuction procedures to be accomplished totally by local anesthesia, thus avoiding the risk of general anesthesia. Such tumescent technique has now become the world wide standard of liposuction procedures.

In contrast, in the present invention, the solute(s) in the tumescent solution are intended to maximize the rate of absorption rather than minimize the same. There are several preferred drugs and clinical means for accelerating the rate of systemic absorption of the tumescent solution. First, the vasodilators methyl nicotinamide, niacin and lidocaine dilate capillaries and thus may act to increase local tissue blood flow and thereby increase the rate of systemic absorption. Second, hyaluronidase is any one of the class of enzymes that may catalyze the depolymerization of hyaluronic acid, thereby reducing the viscosity and rendering tissue containing it more permeable. Third, the tumescent technique, by virtue of the increased interstitial pressure produced by the forcibly injecting a large volume of fluid into the subcutaneous space will accelerate the systemic absorption of the fluid (solvent) and any drugs (solutes) contained therein. Fourth, by heating the tumescent fluid to body temperature, one can avoid vasoconstriction that might result from using a cooler fluid.

BRIEF DESCRIPTION OF THE DRAWINGS

These, as well as other features of the present invention, will become apparent upon reference to the drawings wherein.

DETAILED DESCRIPTION OF THE INVENTION

Figure 1:
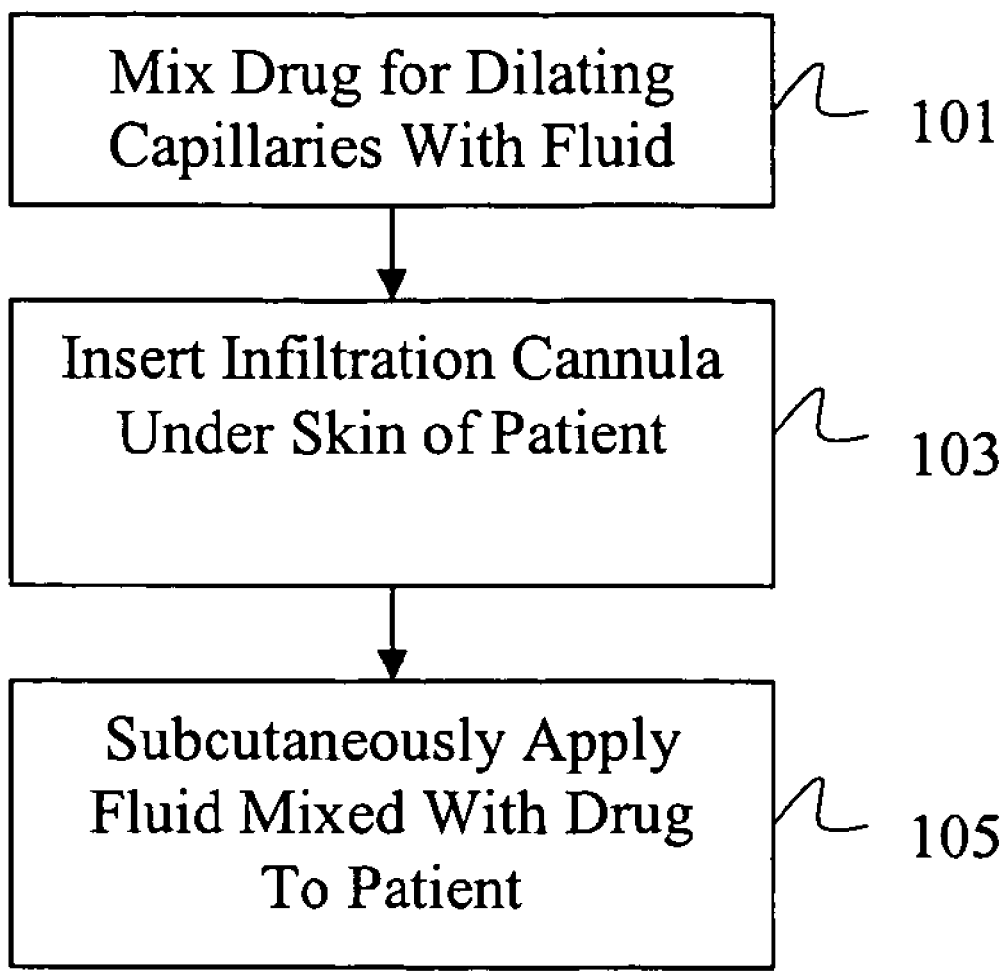
FIG. 1 shows a flow chart of an accelerated subcutaneous absorption provided by the present invention.
Figure 2:
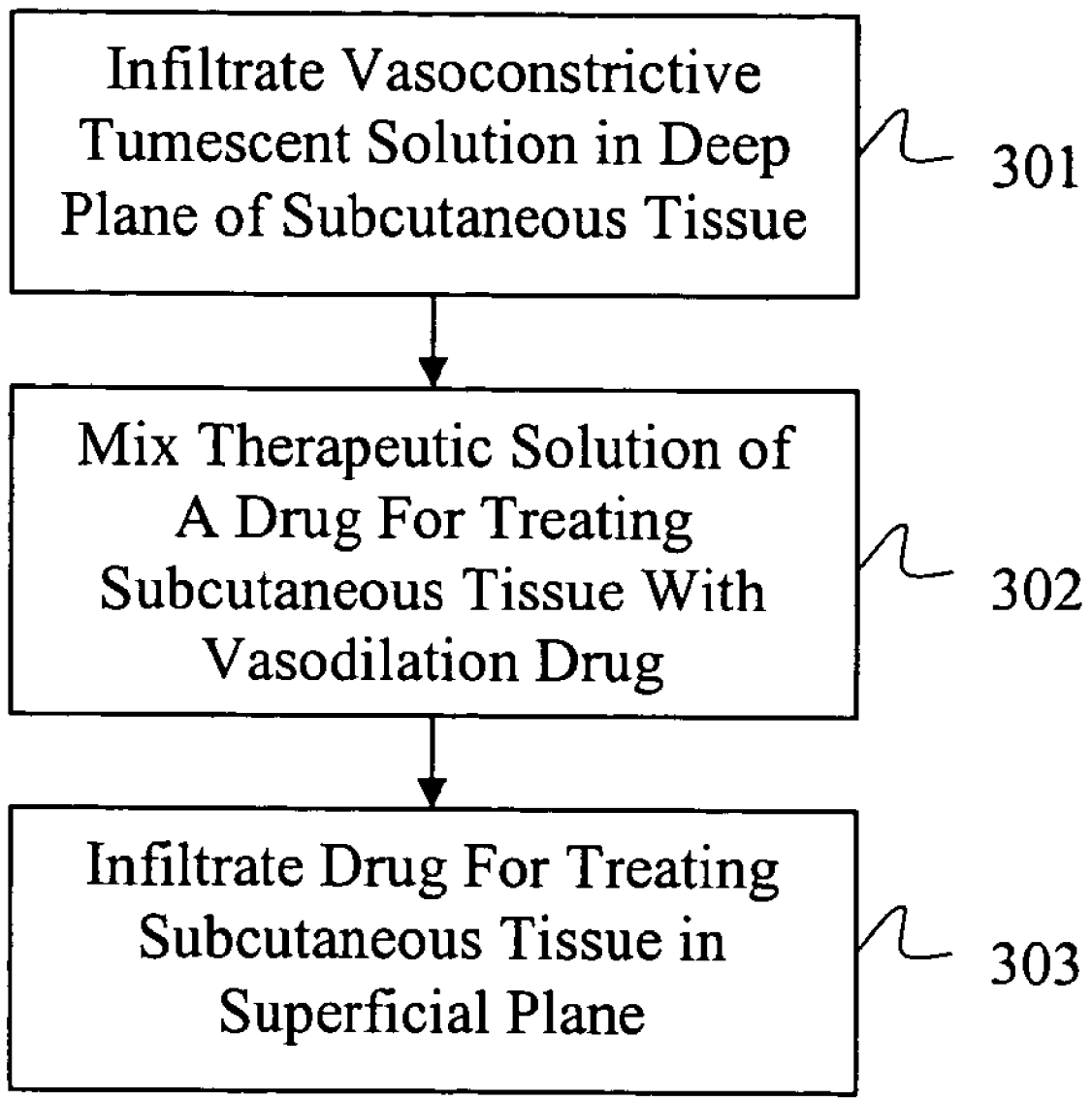
FIG. 2 shows a flow chart of a tumescent technique for increasing subcutaneous absorption rate into specifically targeted tissues, by combining applications of both vasodilator and vasoconstrictive tumescent solution.

Referring now to the drawings wherein the showings are for purpose of illustrating preferred embodiments of the present invention only, and not for purposes of limiting the same, FIG. 1, illustrates the method of the present invention for accelerating subcutaneous absorption. Such method can be applied in various clinical conditions under which accelerated systemic or topical delivery of a specific fluid or drug is required. In addition, the method provided by the present invention can be easily performed by a layman in locations remote from specialized or technically demanding medical equipment without the requirement of special clinical skills. In step 101, a drug that is operative to cause capillary vasodilatation or vasodilatation of subcutaneous blood vessels is mixed with a fluid or a solution of a pharmacologic drug required by the patient.

The fluid or the solution of pharmacologic drug may include a crystalloid solution or a dilute solution of pharmacologic drug such as an antibiotic. The drug used to accelerate the absorption rate of the fluid or the pharmacologic drug is operative to cause capillary vasodilatation, that is, vasodilatation of cutaneous blood vessels. The dilation of capillaries increases the rate of blood flowing through the affected subcutaneous tissue; and consequently, increases the rate of absorption into the systemic circulation of the fluid or pharmacologic drug. As the rate of absorption and circulation of the fluid or pharmacologic drug increases, a clinically significant degree of systemic absorption of the fluid or pharmacologic drug can be achieved without the application of IV access. Currently, many drugs are available to provide the vasodilatation of cutaneous blood vessels of a human body. However, it is appreciated that those drugs which are pharmacologic and potentially toxic to the human bodies are not the appropriate candidates for such drug. For example, although lidocaine is effective to cause dilation of capillaries and increase the rate of blood flowing through affected subcutaneous tissue, which in turn accelerates the absorption rate of drug, it might not be an appropriate candidate for such a drug due to its potentially toxic effect if its concentration is too high. In the preferred embodiment, empirical data shows that topical application of aqueous solution of methyl-nicotinamide or methyl-nicotinate (methyl-nicotinic acid) introduces a very obvious erythema of the affected area of the patient within minutes. As dilute methyl-nicotinamide or methyl-nicotinate does not provide significant toxic effect to the human body, it can thus be used as the drug for accelerating the absorption rate of the pharmacologic drug. It will be appreciated that methyl-nicotinamied or methyl-nicotinate increases local tissue blood flow, but is not the only drug suitable for use in acceleration of systemic absorption. Other drugs that accelerate systemic absorption by other effects can also be used. For example, an enzyme such as hyaluronidase catalyzes depolymerization of hyaluronic acid and thereby reduces the viscosity of the interstitial gel substance and renders the tissue containing it more permeable. Therefore, the rate of systemic absorption can be increased by adding hyaluronidase to the tumescent solution.

In step 103, an infiltration cannula is inserted under the skin of the patient. Although all conventional infiltration cannulas are contemplated herein, preferably, a flexible infiltration cannula is used and inserted into the skin to approach the subcutaneous tissue to be treated. Examples of both rigid and flexible suitable cannulas are disclosed in Applicant's pending U.S. patent application Ser. No. 10/442,370, entitled "Infiltration Cannula" filed May 21, 2003, and pending application entitled "Infiltration Cannula" Ser. No. 10/877,566, filed June 25, the disclosures of which are expressly incorporated herein by reference. In step 105, the fluid or dilute solution of pharmacologic drug mixed with the drug for accelerating the absorption of the pharmacologic drug is injected or infiltrated into the desired subcutaneous tissue under the skin via the infiltration cannula. Therefore, the fluid or dilute solution can be efficiently absorbed by the subcutaneous tissue and delivered to the desired area of the patient.

Under certain clinical conditions, the tumescent technique for accelerating absorption rate can be performed by applications of both vasodilator and vasoconstrictive tumescent solutions in order to direct a drug toward a targeted tissue such as axillary skin and away from other tissues such as systemic circulation. As shown in FIG. 3, when the skin of a patient is to be treated, a vasoconstrictive tumescent solution containing epinephrine (with or without local anesthesia) may be infiltrated in the deep plane of the subcutaneous tissue of the patient in step 301. A therapeutic tumescent solution of a drug for treating the skin is then infiltrated in the superficial plane located above the deep plane in step 303. By the infiltration of the vasoconsctrictive tumescent solution, the deep plane of tumescent subcutaneous tissue acts as a buffer or barricade that prevents or delays absorption of the drug into deeper highly vascular tissue. When a large area of the skin is to be treated, or when acceleration of the drug absorption rate is required, the therapeutic tumescent solution drug is mixed with a vasodialator drug or a drug increasing bulk flow of the drug as mentioned above in step 302. Alternatively, for the treatments of deep tissues, organs and internal viscera, a vasoconstrictive tumescent solution is applied superficially or peripherally relative to the tissue or organ, while the therapeutic tumescent solution containing a drug for treating the deep tissues is applied deeply or adjacent to or into the tissue or organ. Again, when a large area of deep tissues is to be treated, a drug for increasing absorption rate of the drug is mixed with the therapeutic tumescent solution.

The scope of this disclosure is not limited by these exemplary embodiments. Numerous variations, whether explicitly provided for by the specification or implied by the specification, such as variations in shape, structure, dimension, type of material or manufacturing process may be implemented by one of skill in the art in view of this disclosure.

What is claimed is:

1. A method of increasing absorption rate of a therapeutic drug, comprising:
    applying a first solution in a first level under skin of a patient, wherein the first solution contains a therapeutic drug for treating subcutaneous tissue of the patient; and
    applying a second solution in a second level under the skin of the patient, wherein the second solution contains a vasoconstrictive drug; wherein
    the second level is deeper than the first level to serve as a buffer for preventing or delaying absorption of the therapeutic drug into deep vascular tissue.

2. The method of claim 1, wherein the first solution further contains a vasodilation drug.

3. The method of claim 1, wherein the vasoconstrictive drug includes epinephrine.

4. The method of claim 1, wherein the first level includes a deep plane of the subcutaneous tissue, and the second level includes a superficial plane immediately below dermis of the patient.

5. A method of increasing absorption rate of a therapeutic drug, comprising:
    applying a first solution in a first level under the skin of a patient, wherein the first solution contains a therapeutic drug for treating the skin of the patient; and
    applying a second solution in a second level under the skin of the patient, wherein the second solution contains a vasoconstrictive drug only; wherein
    the first level is deeper than the second level to serve as a buffer for preventing or delaying absorption of the therapeutic drug into superficial region of the skin.

6. The method of claim 5, wherein the first solution further contains a vasodilation drug.

7. The method of claim 6, wherein the vasoconstrictive drug comprises epinephrine.

\* \* \* \* \*